United States Patent [19]

Labedz et al.

[11] Patent Number: 6,072,778
[45] Date of Patent: Jun. 6, 2000

[54] METHOD OF CONTROLLING A COMMUNICATION SYSTEM

[75] Inventors: Gerald P. Labedz, Chicago; Robert T. Love, Barrington, both of Ill.

[73] Assignee: Motorola, Inc., Schaumburg, Ill.

[21] Appl. No.: 08/702,423

[22] Filed: Aug. 14, 1996

[51] Int. Cl.[7] .............................. H04B 7/26; H04J 3/14; H04J 13/00
[52] U.S. Cl. .................. 370/252; 370/335; 445/510; 445/522
[58] Field of Search .................... 370/230, 252, 370/328, 329, 331, 332, 333, 335, 342, 441, 479; 455/422, 450, 453, 522, 510, 63; 375/200, 206

[56] References Cited

U.S. PATENT DOCUMENTS

| | | | |
|---|---|---|---|
| 5,604,730 | 2/1997 | Tiedemann, Jr. | 370/252 |
| 5,666,356 | 9/1997 | Fleming et al. | 370/328 |
| 5,671,218 | 9/1997 | I et al. | 370/252 |
| 5,734,646 | 3/1998 | I et al. | 370/335 |
| 5,796,722 | 8/1998 | Kotzin et al. | 370/252 |

OTHER PUBLICATIONS

D. Liu and M. E. Zarki, "SIR–Based Call Admission Control for DS–CDMA Cellular Systems," IEEE Communications, vol. 12, No. 4, pp. 638–644, May 1994.

*Primary Examiner*—Ricky Ngo
*Attorney, Agent, or Firm*—Richard A. Sonnentag

[57] ABSTRACT

A code division multiple access (CDMA) communication system (100) has improved control by accurately characterizing coverage and loading parameters related to the CDMA communication system (100). To accurately characterize coverage and loading parameters related to the CDMA communication system, parameter meshes corresponding to parameters of the CDMA communication system are generated. The parameter meshes are evaluated, either individually or in combination, to provide comprehensive information regarding the performance of the CDMA communication system. Based on the results of the evaluation, a controller (113) within the CDMA communication system (100) controls the parameters to improve call quality, loading, etc. of the CDMA communication system (100).

4 Claims, 5 Drawing Sheets

6,072,778

METHOD OF CONTROLLING A COMMUNICATION SYSTEM

FIELD OF THE INVENTION

The present invention relates generally to communication systems, and more particularly to accurately characterizing coverage and loading for improved communication system control.

BACKGROUND OF THE INVENTION

The performance of fast power controlled cellular multiple access systems where large numbers of users share the same carrier frequency, such as code division multiple access (CDMA) communication systems, are not well characterized and/or controlled by prior art techniques. The reason is due to the many nuances presented by such a CDMA communication system. For example, unlike conventional cellular multiple access systems, in a CDMA communication system as power is shared on the carrier among the users, adjustments take place which constantly change both base-station and mobile station transmit powers, and hence the noise seen at both the base-station and mobile station change many times per second over a wide range. Another reason is that localized delay spread conditions can profoundly affect both the sensitivity performance of the receivers in the CDMA communication system, and also, in turn, affect the power control settings at each base-station and mobile station.

Related to the above is the fact that radio performance and transmit power are profoundly affected by the feature of soft handoff, where a mobile station may transmit to, and receive signals from, multiple base-stations. Another reason is that the previous methods take no account of the practical fact that, during communication, many mobile stations are not connected to the best base-stations but, due to timers and realistic scan measurement times, often experience less than optimal connections for communication. This affects the amount of noise seen by CDMA receivers in the system and in turn the power control settings at the base-station.

Thus, a need exists for an accurate method of characterizing coverage and loading in a CDMA communication system to provide improved system control.

DETAILED DESCRIPTION OF A PREFERRED EMBODIMENT

Figure 1:
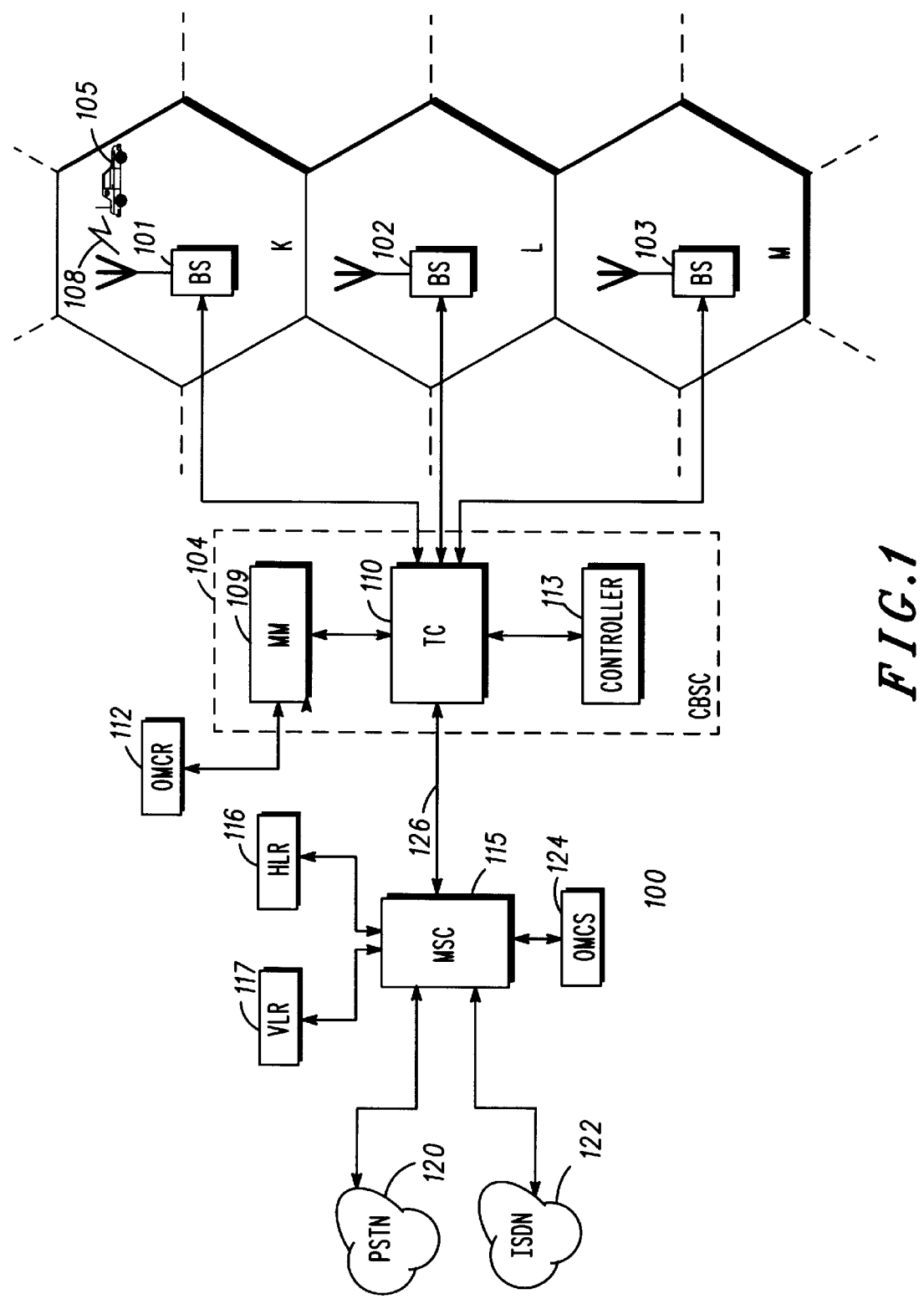
FIG. 1 generally depicts, in block diagram form, a code-division multiple access (CDMA) wireless communication system which may beneficially employ improved system control in accordance with the invention.

Stated generally, a code division multiple access (CDMA) communication system has improved control by accurately characterizing coverage and loading parameters related to the CDMA communication system. To accurately characterize coverage and loading parameters related to the CDMA communication system, parameter meshes corresponding to parameters of the CDMA communication system are generated. The parameter meshes are evaluated, either individually or in combination, to provide comprehensive information regarding the performance of the CDMA communication system. Based on the results of the evaluation, a controller within the CDMA communication system controls the parameters to improve call quality, loading, etc. of the CDMA communication system.

More specifically, a method of controlling a communication system is disclosed. The method generally comprises the steps of calculating at least one parameter mesh corresponding to a parameter related to the communication system then evaluating the parameter mesh to generate a control signal effecting the parameter related to the communication system. The communication system is controlled based on the generated control signal. In the preferred embodiment, the parameter related to the communication system includes, but is not limited to, forward and reverse power requirements, the number of useful pilot signals, and the best pilot signal. Also in the preferred embodiment, the calculation of the parameter mesh is performed at each x,y coordinate of a grid over an area of interest.

In an alternate version of CDMA communication system control, the forward link power requirements for all base-stations in an area of interest are determined. Then, based on the determined forward link power requirements, the base-station which contributes the largest forward link power is determined. To mitigate the effects of this base-station, the number of mobile station connections to that base-station are limited so that its forward link power contribution with respect to the total forward link power of all base-stations is diminished. The number of connections to the base-station of interest are allowed to increase based on a re-evaluation of the base-station's effect on the communication system.

In another version of CDMA communication system control, the total amount of noise contributed by mobile stations in the communication system is determined. Next, the mobile stations which contribute an unacceptable amount of noise to the determined total amount of noise are then determined. Finally, access to those mobile stations which contribute an unacceptable amount of noise until the total noise in the communication system reaches an acceptable level is limited to diminish the effects of the offensive mobile stations. In this version of CDMA communication system control, the total noise in the CDMA communication system is determined via a required reverse link power requirement parameter mesh calculated for all mobile stations in an area of interest.

FIG. 1 generally depicts, in block diagram form, a wireless communication system 100 which may beneficially employ improved system control in accordance with the invention. In the preferred embodiment, the wireless communication system 100 is a code-division multiple access (CDMA) cellular radiotelephone system. As one of ordinary skill in the art will appreciate, however, the improved system control in accordance with the invention can be implemented in any wireless communication system.

Referring to FIG. 1, acronyms are used for convenience. The following is a list of definitions for the acronyms used in FIG. 1:

| | |
|---|---|
| PSTN | Public Switched Telephone Network |
| ISDN | Integrated Services Digital Network |
| MSC | Mobile Switching Center |
| VLR | Visitor Location Register |
| HLR | Home Location Register |
| OMCS | Operations and Maintenance Center - Switch |
| OMCR | Operations and Maintenance Center - Radio |
| CBSC | Centralized Base Station Controller |
| TC | Transcoder |
| MM | Mobility Manager |
| CONT | Controller |
| BS | Base-Station |
| MS | Mobile Station |

As seen in FIG. 1, multiple base-stations 101–103 are coupled to a CBSC 104. Each base-station 101–103 provides radio frequency (RF) communication to a mobile station 105. In the preferred embodiment, the transmitter/receiver (transceiver) hardware implemented in the base-stations 101–103 and the mobile stations 105 to support conveyance of the RF communication resource is substantially defined in the document titled by TIA/EIA/IS-95A, July 1993, available from the Telecommunication Industry Association (TIA), 2001 Pennsylvania Ave., Washington, D.C., 20006. The CBSC 104 is responsible for, inter alia, call processing via the TC 110 and mobility management via the MM 109. The CBSC 104 likewise contains a controller 113 which provides improved system control in accordance with the invention. Other tasks of the CBSC 104 include feature control and transmission/networking interfacing. For more information on the general functionality of the CBSC 104, reference is made to U.S. Pat. No. 5,475,686 to Bach et al., assigned to the assignee of the present application, and incorporated herein by reference.

Also depicted in FIG. 1 is an OMCR 112 coupled to the MM 109 of the CBSC 104. The OMCR 112 is responsible for the operations and general maintenance of the radio portion (CBSC 104 and base-station 101–103 combination) of the communication system 100. The CBSC 104 is coupled to a MSC 115 which provides switching capability between the PSTN 120/ISDN 122 and the CBSC 104. The OMCS 124 is responsible for the operations and general maintenance of the switching portion (MSC 115) of the communication system 100. The HLR 116 and VLR 117 provide the communication system 100 with user information primarily used for billing purposes.

The functionality of the CBSC 104, MSC 115, HLR 116 and VLR 117 is shown in FIG. 1 as distributed, however one of ordinary skill in the art will appreciate that the functionality could likewise be combined into a single element. Also, for different configurations, the TC 110 could be located at either the MSC 115 or a base-station 101–103. The link 126 coupling the MSC 115 with the CBSC 104 is a T1/E1 link which is well known in the art. By placing the TC 110 at the CBSC, a 4:1 improvement in link budget is realized due to compression of the input signal (input from the T1/E1 link 126) by the TC 110. The compressed signal is transferred to a particular base-station 101–103 for transmission to a particular mobile station 105. Important to note is that the compressed signal transferred to a particular base-station 101–103 undergoes further processing at the base-station 101–103 before transmission occurs. Put differently, the eventual signal transmitted to the mobile station 105 is different in form but the same in substance as the compressed signal exiting the TC 110.

When the mobile station 105 receives the signal transmitted by a base-station 101–103, the mobile station 105 will essentially "undo" (commonly referred to as "decode") most of the processing performed by the system 100. When the mobile station 105 transmits a signal back to a base-station 101–103, the mobile station 105 likewise implements its own processing. After a signal having undergone processing is transmitted by the mobile station 105 (the processing of the signal is to change the form, but not the substance, of the signal) to a base-station 101–103, the base-station 101–103 will "undo" the processing performed on the signal and transfer to the appropriate point within the system 100. Eventually, the signal will be transferred to an end user via the T1/E1 link 126.

Figure 2:
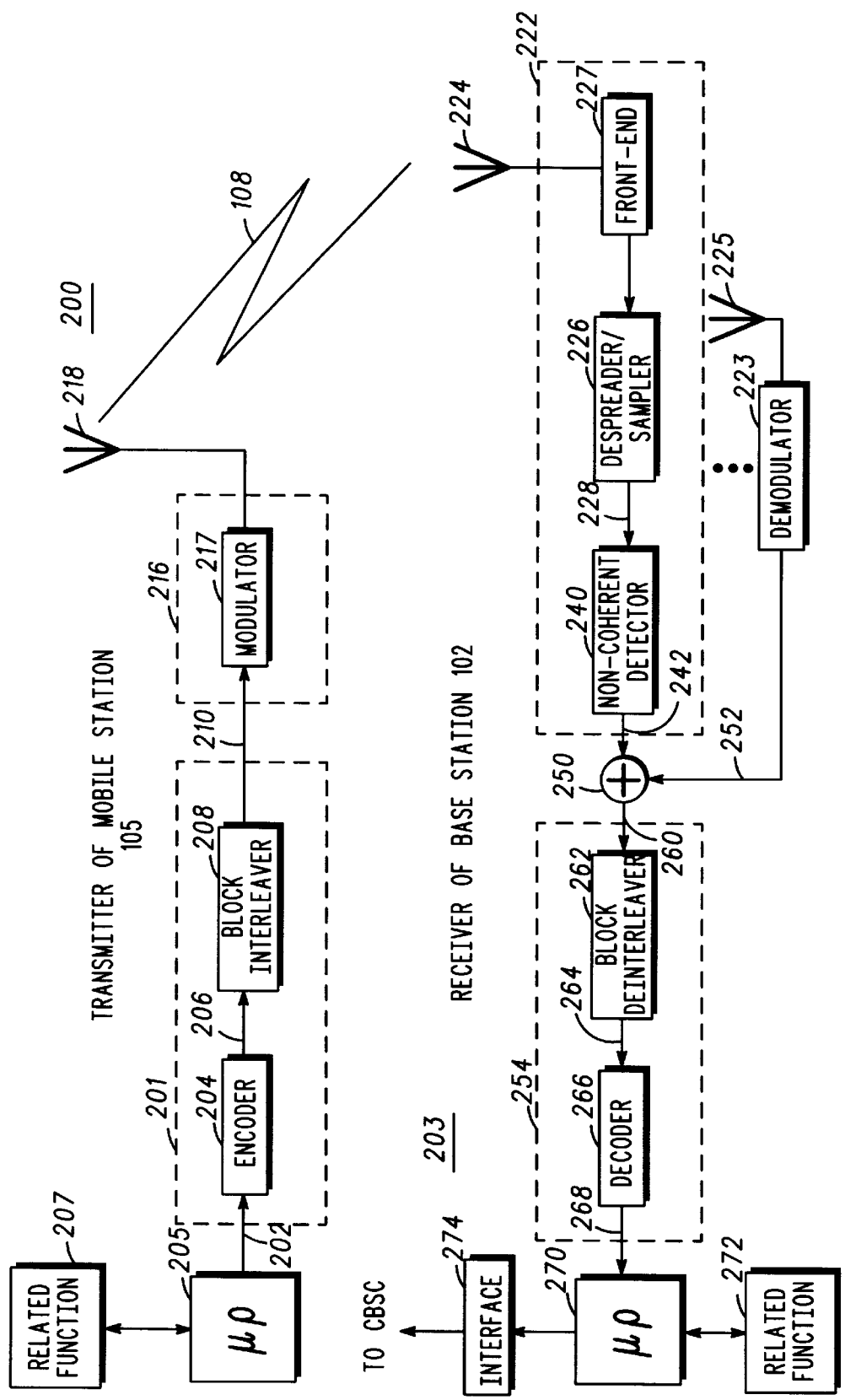
FIG. 2 generally depicts, in block diagram form, a transmitter of a CDMA mobile station in communication with a CDMA receiver of a base-station.

FIG. 2 generally depicts, in block diagram form, a transmitter 200 of a CDMA mobile station 105 in communication with a receiver 203 of any one (or all) of CDMA base-stations 101–103. In the encoding portion 201 of the communication system, traffic channel data bits 202 originate from a microprocessor ($\mu$P) 205, and are input to an encoder 204 at a particular bit rate (e.g., 9.6 kilobit/second). The $\mu$P 205 is coupled to a block designated related functions 207, where functions including call processing, link establishment, and other general functions related to establishing and maintaining wireless communication are performed. The traffic channel data bits 202 can include either voice converted to data by a vocoder, pure data, or a combination of the two types of data. Encoder 204 encodes the traffic channel data bits 202 into data symbols 206 at a fixed encoding rate (1/r) with an encoding algorithm which facilitates subsequent maximum likelihood decoding of the data symbols into data bits (e.g., convolutional or block coding algorithms). For example, encoder 204 encodes traffic channel data bits 202 (e.g., 192 input data bits that were received at a rate of 9.6 kilobits/second) at a fixed encoding rate of one data bit to three data symbols (i.e., ⅓) such that the encoder 204 outputs data symbols 206 (e.g., 576 data symbols output at a 28.8 kilo symbols/second rate).

The data symbols 206 are then input into an interleaver 208. Interleaver 208 organizes the data symbols 206 into blocks (i.e., frames) and block interleaves the input data symbols 206 at the symbol level. In the interleaver 208, the data symbols are individually input into a matrix which defines a predetermined size block of data symbols. The data symbols are input into locations within the matrix so that the matrix is filled in a column by column manner. The data symbols are individually output from locations within the matrix so that the matrix is emptied in a row by row manner. Typically, the matrix is a square matrix having a number of rows equal to the number of columns; however, other matrix forms can be chosen to increase the output interleaving distance between the consecutively input non-interleaved data symbols. The interleaved data symbols 110 are output by the interleaver 208 at the same data symbol rate that they were input (e.g., 28.8 kilo symbols/second). The predetermined size of the block of data symbols defined by the matrix is derived from the maximum number of data symbols which can be transmitted at a coded bit rate within a predetermined length transmission block. For example, if data symbols 206 are output from the encoder 204 at a 28.8 kilo symbols/second rate, and if the predetermined length of the transmission block is 20 milliseconds, then the predetermined size of the block of data symbols is 28.8 kilo symbols/second times 20 milliseconds (ms) which equals 576 data symbols which defines a 18 by 32 matrix.

The encoded, interleaved data symbols 210 are output from encoding portion 201 of the communication system and input to a transmitting portion 216 of the communication system. The data symbols 210 are prepared for transmission over a communication channel by a modulator 217. Subsequently, the modulated signal is provided to an antenna 218 for transmission over the digital radio channel 108.

The modulator 217 prepares the data symbols 210 for direct sequence CDMA transmission by deriving a sequence of fixed length codes from the encoded, interleaved data symbols 210 in a spreading process. For example, the data symbols within the stream of reference-coded data symbols 210 may be spread to a unique fixed length code such that a group of six data symbols is represented by a single 64 bit length code. The codes representing the group of six data symbols preferably are combined to form a single 64 bit length code. As a result of this spreading process, the modulator 217 which received the encoded, interleaved data symbols 210 at a fixed rate (e.g., 28.8 kilo symbols/second) now has a spread sequence of 64 bit length codes having a higher fixed symbol rate (e.g., 307.2 kilo symbols/second). It will be appreciated by those skilled in the art that the data symbols within the stream of encoded, interleaved data bits 210 may be spread according to numerous other algorithms into a sequence of larger length codes.

The spread sequence is further prepared for direct sequence code divided spread-spectrum transmission by further spreading the spread sequence with a long spreading code (e.g., PN code). The spreading code is a user specific sequence of symbols or unique user code which is output at a fixed chip rate (e.g., 1.228 Megachips/second). In addition to providing an identification as to which user sent the encoded traffic channel data bits 202 over the digital radio channel 108, the unique user code enhances the security of the communication in the communication channel by scrambling the encoded traffic channel data bits 202. In addition, the user code spread encoded data bits (i.e., data symbols) are used to bi-phase modulate a sinusoid by driving the phase controls of the sinusoid. The sinusoid output signal is bandpass filtered, translated to an RF frequency, amplified, filtered and radiated by an antenna 218 to complete transmission of the traffic channel data bits 202 in a digital radio channel 108 with Binary Phase Shift Keyed (BPSK) modulation.

A receiving portion 222 of the base station receiver 203 receives the transmitted spread-spectrum signal from over the digital radio channel 108 through antenna 224. The received signal is input into a receiver front-end 221 which includes circuitry to downconvert the digital radio channel 108 into a signal suitable for sampling. The output of the receiver front-end 221 is sampled into data samples by despreader and sampler 226. Subsequently, the data samples 242 are output to the decoding portion 254 of the communication system.

The despreader and sampler 226 preferably BPSK samples the received spread-spectrum signal by filtering, demodulating, translating from the RF frequencies, and sampling at a predetermined rate (e.g., 1.2288 Megasamples/second). Subsequently, the BPSK sampled signal is despread by correlating the received sampled signals with the long spreading code. The resulting despread sampled signal 228 is sampled at a predetermined rate and output to a non-coherent detector 240 (e.g., 307.2 kilo samples/second so that a sequence of four samples of the received spread-spectrum signal is despread and/or represented by a single data sample) for later non-coherent detection of data samples 242.

As will be appreciated by those skilled in the art, multiple receiving portions 222 through 223 and antennae 224 through 225, respectively, can be used to achieve space diversity. The Nth receiver portion would operate in substantially the same manner to retrieve data samples from the received spread-spectrum signal in digital radio channel 108 as the above described receiving portion 222. The outputs 242 through 252 of the N receiving portions preferably are input to a summer 250 which diversity combines the input data samples into a composite stream of coherently detected data samples 260.

The individual data samples 260 which form soft decision data are then input into a decoding portion 254 including a deinterleaver 262 which deinterleaves the input soft decision data 260 at the individual data level. In the deinterleaver 262, the soft decision data 260 are individually input into a matrix which defines a predetermined size block of soft decision data. The soft decision data are input into locations within the matrix so that the matrix is filled in a row by row manner. The deinterleaved soft decision data 264 are individually output from locations within the matrix so that the matrix is emptied in a column by column manner. The deinterleaved soft decision data 264 are output by the deinterleaver 262 at the same rate that they were input (e.g., 28.8 kilo symbols/second).

The predetermined size of the block of soft decision data defined by the matrix is derived from the maximum rate of sampling data samples from the spread-spectrum signal received within the predetermined length transmission block.

The deinterleaved soft decision data 264, are input to a decoder 266 which uses maximum likelihood decoding techniques to generate estimated traffic channel data bits 268. The maximum likelihood decoding techniques may be augmented by using an algorithm which is substantially similar to a Viterbi decoding algorithm. The decoder 266 uses a group of the individual soft decision data 264 to form a set of soft decision transition metrics for use at each particular time state of the maximum likelihood sequence estimation decoder 266. The number of soft decision data 264 in the group used to form each set of soft decision transition metrics corresponds to the number of data symbols 206 at the output of the convolutional encoder 204 generated from each input data bit 202. The number of soft decision transition metrics in each set is equal to two raised to the power of the number of soft decision data 264 in each group. For example, when a ⅓ convolutional encoder is used in the transmitter, three data symbols 105 are generated from each input data bit 202. Thus, decoder 266 uses groups of three individual soft decision data 264 to form eight soft decision transition metrics for use at each time state in the maximum likelihood sequence estimation decoder 266. The estimated traffic channel data bits 268 are generated at a rate related to the rate that the soft decision data 264 are input to the decoder 266 and the fixed rate used to originally encode the input data bits 202 (e.g., if the soft decision data are input at 28.8 kilometrics/second and the original encoding rate was ⅓ then estimated traffic channel data bits 268 are output at a rate of 9600 bits/second).

The estimated traffic channel data bits 268 are input into a $\mu P$ 270, which is similar to $\mu P$ 207. As in the case of $\mu P$ 207, the $\mu P$ 270 is coupled to a block designated related functions 272, this block also performing functions including call processing, link establishment, and other general functions related to establishing and maintaining wireless communication. The $\mu P$ 270 is also coupled to an interface 274, which allows the receiver 203 of the base station 103 to communicate with the CBSC 113.

Figure 3:
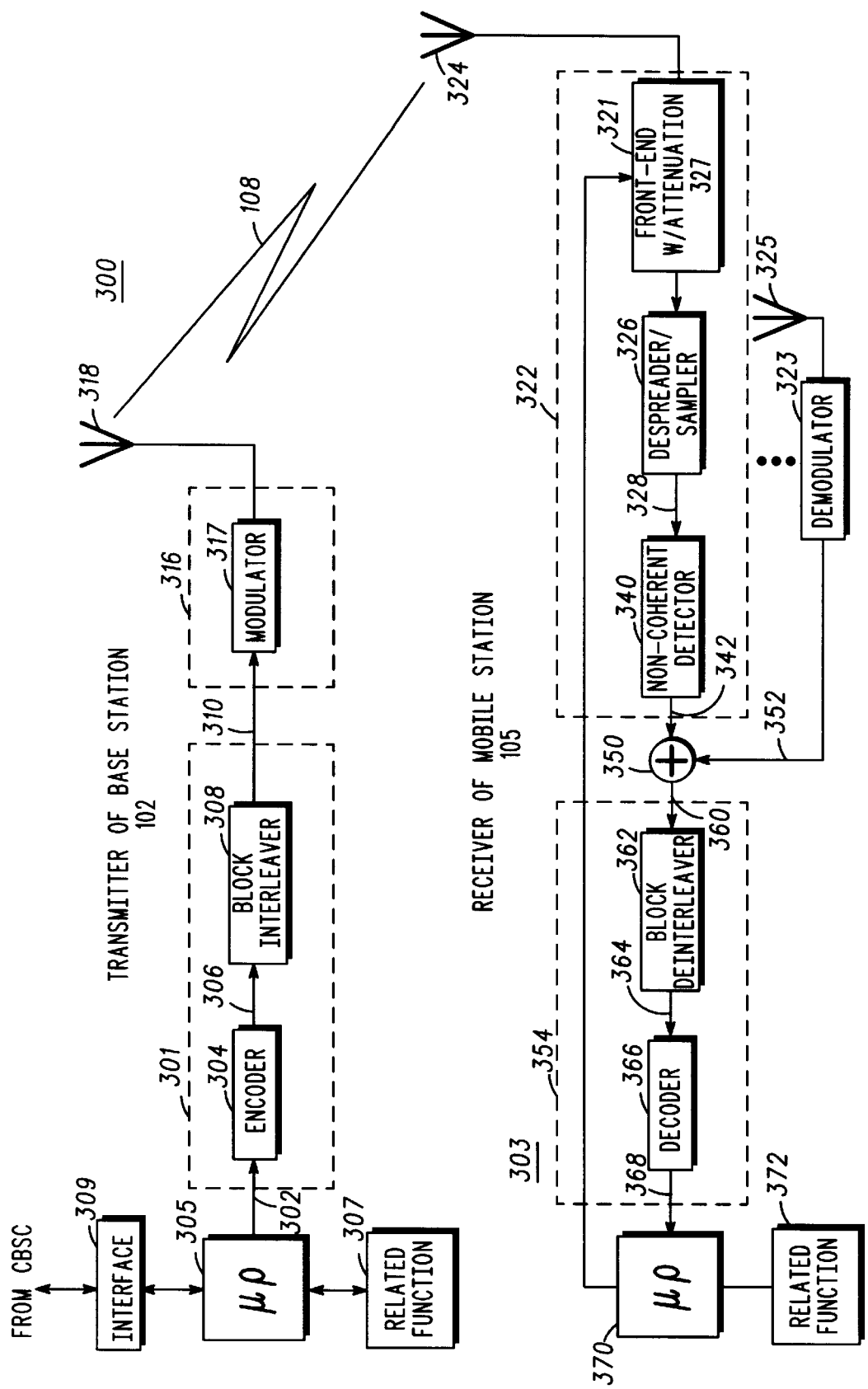
FIG. 3 generally depicts, in block diagram form, a transmitter of a CDMA base-station in communication with a receiver of a CDMA mobile station.

FIG. 3 generally depicts a transmitter 300 of any one of CDMA base-stations 101–103 in communication with a receiver 303 of a CDMA mobile station 105. In the encoding portion 301 of the communication system, traffic channel data bits 302 are output from a μP 305, and are input to an encoder 304 at a particular bit rate (e.g., 9.6 kilobit/second). The μP 305 is coupled to a block designated related functions 307, which performs similar wireless-related functions as blocks 207 and 272 of FIG. 2. The μP 305 is also coupled to an interface 309 which allows the transmitter 300 of base station 102 to communicate with the CBSC 114.

The traffic channel data bits 302 can include either voice converted to data by a vocoder, pure data, or a combination of the two types of data. Encoder 304 encodes the traffic channel data bits 302 into data symbols 306 at a fixed encoding rate (1/r) with an encoding algorithm which facilitates subsequent maximum likelihood decoding of the data symbols into data bits (e.g., convolutional or block coding algorithms). For example, encoder 304 encodes traffic channel data bits 302 (e.g., 192 input data bits that were received at a rate of 9.6 kilobits/second) at a fixed encoding rate of one data bit to two data symbols (i.e., ½) such that the encoder 304 outputs data symbols 306 (e.g., 384 data symbols output at a 19.2 kilo symbols/second rate).

The data symbols 306 are then input into an interleaver 308. Interleaver 308 organizes the data symbols 306 into blocks (i.e., frames) and block interleaves the input data symbols 306 at the symbol level. In the interleaver 308, the data symbols are individually input into a matrix which defines a predetermined size block of data symbols. The data symbols are input into locations within the matrix so that the matrix is filled in a column by column manner. The data symbols are individually output from locations within the matrix so that the matrix is emptied in a row by row manner. Typically, the matrix is a square matrix having a number of rows equal to the number of columns; however, other matrix forms can be chosen to increase the output interleaving distance between the consecutively input non-interleaved data symbols. The interleaved data symbols 310 are output by the interleaver 308 at the same data symbol rate that they were input (e.g., 19.2 kilo symbols/second). The predetermined size of the block of data symbols defined by the matrix is derived from the maximum number of data symbols which can be transmitted at a coded bit rate within a predetermined length transmission block. For example, if data symbols 306 are output from the encoder 304 at a 19.2 kilo symbols/second rate, and if the predetermined length of the transmission block is 20 milliseconds, then the predetermined size of the block of data symbols is 19.2 kilo symbols/second times 20 milliseconds (ms) which equals 384 data symbols which defines a 18 by 32 matrix.

The encoded, interleaved data symbols 310 are output from encoding portion 301 of the communication system and input to a transmitting portion 316 of the communication system. The data symbols 310 are prepared for transmission over a communication channel by a modulator 317. Subsequently, the modulated signal is provided to an antenna 318 for transmission over the digital radio channel 108.

The modulator 317 prepares the data symbols 310 for direct sequence code divided spread-spectrum transmission by performing data scrambling on the encoded, interleaved data symbols 310. Data scrambling is accomplished by performing the modulo-2 addition of the interleaver output symbols 310 with the binary value of a long code pseudo-noise PN chip that is valid at the start of the transmission period for that symbol. This pseudo-noise PN sequence is the equivalent of the long code operating at 1.2288 MHz clock rate, where only the first output of every 64 is used for the data scrambling (i.e., at a 19200 sample per second rate).

After scrambling, a sequence of fixed length codes from the scrambled data symbols are derived in a spreading process. For example, each data symbol within the stream of scrambled data symbols may preferably be spread to a unique fixed length code such that each data symbol is represented by a single 64 bit length code. The code representing the data symbol preferably is modulo-2 added to the respective data symbol. As a result of this spreading process, the modulator 317 which received the encoded, interleaved data symbols 310 at a fixed rate (e.g., 19.2 kilo symbols/second) now has a spread sequence of 64 bit length codes having a higher fixed symbol rate (e.g., 1228.8 kilo symbols/second). It will be appreciated by those skilled in the art that the data symbols within the stream of encoded, interleaved data bits 310 may be spread according to numerous other algorithms into a sequence of larger length codes without departing from the scope and spirit of the present invention.

The spread sequence is further prepared for direct sequence code divided spread-spectrum transmission by further spreading the spread sequence with a long spreading code (e.g., PN code). The spreading code is a user specific sequence of symbols or unique user code which is output at a fixed chip rate (e.g., 1.2288 Megachips/second). In addition to providing an identification as to which user sent the encoded traffic channel data bits 302 over the digital radio channel 308, the unique user code enhances the security of the communication in the communication channel by scrambling the encoded traffic channel data bits 302. In addition, the user code spread encoded data bits (i.e., data symbols) are used to bi-phase modulate a sinusoid by driving the phase controls of the sinusoid. The sinusoid output signal is bandpass filtered, translated to an RF frequency, amplified, filtered and radiated by an antenna 318 to complete transmission of the traffic channel data bits 302 in a digital radio channel 108 with BPSK modulation.

When a CDMA wireless communication system is designed to overlay over an existing wireless communication system (for example, an AMPS wireless communication system), it is necessary to anticipate and minimize any intersystem interference which might result from the deployment. There are several potential intersystem interference mechanisms, but the dominant problem is an interference product resulting from strong AMPS base-station transmissions mixing in the front-end of a CDMA mobile station 105 which creates undesired signals appearing inside the passband of the CDMA mobile station 105.

Still referring to FIG. 3, a receiving portion 322 of the mobile station receiver 303 receives the transmitted spread-spectrum signal from the digital radio channel 108 through antenna 324. In the preferred embodiment, the receiver 303 is a RAKE receiver which is well known in the art. The received signal is input into a receiver front-end 321 which includes circuitry to downconvert the digital radio channel 108 into a signal suitable for sampling. The receiver front-end 321 also includes an attenuator 327 (not shown) which is used to mitigate the effects of AMPS interference as described above. As is well known in the art, the attenuator 327 located at the front-end 321 of the receiver 303 will reduce the desired (CDMA) signal by the corresponding amount of attenuation, but will reduce the undesired IM products generated in the receiver 200 by three (3) times the amount of attenuation. As such, by selectively enabling and disabling the attenuator, the effects of the interfering AMPS signals are mitigated to the point where call quality is improved and the likelihood of dropping a call is significantly diminished.

Still referring to FIG. 3, the output of the receiver front-end 321 is sampled into data samples by despreader and sampler 326. Subsequently, the data samples 342 are output to the decoding portion 354 of the communication system. The despreader and sampler 326 preferably BPSK samples the received spread-spectrum signal by filtering, demodulating, translating from the RF frequencies, and sampling at a predetermined rate (e.g., 1.2288 Megasamples/second). Subsequently, the BPSK sampled signal is despread by correlating the received sampled signals with the long spreading code. The resulting despread sampled signal 328 is sampled at a predetermined rate and output to a non-coherent detector 340 (e.g., 19.2 kilo samples/second so that a sequence of 64 samples of the received spread-spectrum signal is despread and/or represented by a single data sample) for non-coherent detection of data samples 342.

As will be appreciated by those skilled in the art, multiple receiving portions 322 through 323 and antennae 324 through 325, respectively, can be used to achieve space diversity. The Nth receiver portion would operate in substantially the same manner to retrieve data samples from the received spread-spectrum signal in digital radio channel 320 as the above described receiving portion 322. The outputs 342 through 352 of the N receiving portions preferably are input to a summer 350 which diversity combines the input data samples into a composite stream of coherently detected data samples 360.

The individual data samples 360 which form soft decision data are then input into a decoding portion 354 including a deinterleaver 362 which deinterleaves the input soft decision data 360 at the individual data level. In the deinterleaver 362, the soft decision data 360 are individually input into a matrix which defines a predetermined size block of soft decision data. The soft decision data are input into locations within the matrix so that the matrix is filled in a row by row manner. The deinterleaved soft decision data 364 are individually output from locations within the matrix so that the matrix is emptied in a column by column manner. The deinterleaved soft decision data 364 are output by the deinterleaver 362 at the same rate that they were input (e.g., 19.2 kilometrics/second).

The predetermined size of the block of soft decision data defined by the matrix is derived from the maximum rate of sampling data samples from the spread-spectrum signal received within the predetermined length transmission block.

The deinterleaved soft decision data 364, are input to a decoder 366 which uses maximum likelihood decoding techniques to generate estimated traffic channel data bits 368. The maximum likelihood decoding techniques may be augmented by using an algorithm which is substantially similar to a Viterbi decoding algorithm. The decoder 366 uses a group of the individual soft decision data 364 to form a set of soft decision transition metrics for use at each particular time state of the maximum likelihood sequence estimation decoder 366. The number of soft decision data 364 in the group used to form each set of soft decision transition metrics corresponds to the number of data symbols 306 at the output of the convolutional encoder 304 generated from each input data bit 302. The number of soft decision transition metrics in each set is equal to two raised to the power of the number of soft decision data 364 in each group. For example, when a ½ convolutional encoder is used in the transmitter, two data symbols 306 are generated from each input data bit 302. Thus, decoder 366 uses groups of two individual soft decision data 364 to form two soft decision transition metrics for use at each time state in the maximum likelihood sequence estimation decoder 366. The estimated traffic channel data bits 368 are generated at a rate related to the rate that the soft decision data 364 are input to the decoder 366 and the fixed rate used to originally encode the input data bits 302 (e.g., if the soft decision data are input at 19.2 kilometrics/second and the original encoding rate was ½ then estimated traffic channel data bits 368 are output at a rate of 9600 bits/second). The estimated traffic channel data bits 368 are input into a $\mu P$ 370 which interprets the estimated traffic channel data bits 368 and other fields. The $\mu P$ 370 is also coupled to the front-end 321 via the control line 371. Based on a command from the base-station 102, the $\mu P$ 370 will enable/disable the attenuator 327 in accordance with the invention. The $\mu P$ 370 is further coupled to related functions 372 which performs wireless-related functions similar to those performed by blocks 207, 272 and 307.

To implement improved system control in accordance with the invention, a calculation of parameter meshes is first performed in the controller 113 of FIG. 1. A parameter mesh is simply the calculation of a particular parameter related to the communication system at each x,y coordinate of a grid over the area of interest. This can be seen in FIG. 4, where the area of interest is defined by the points $x_s, y_s$. In the preferred embodiment, the parameter meshes are calculated over the entire region repeatedly for a number of different conditions to form a mesh set, and the mesh set can be utilized for improved system control in accordance with the invention as will be explained hereinafter.

A short summary of the types of parameters which can be calculated by the controller 113 in accordance with the invention at this point is instructive.

Forward Link (Base-station to Mobile Station) Power Requirement

Figure 4:
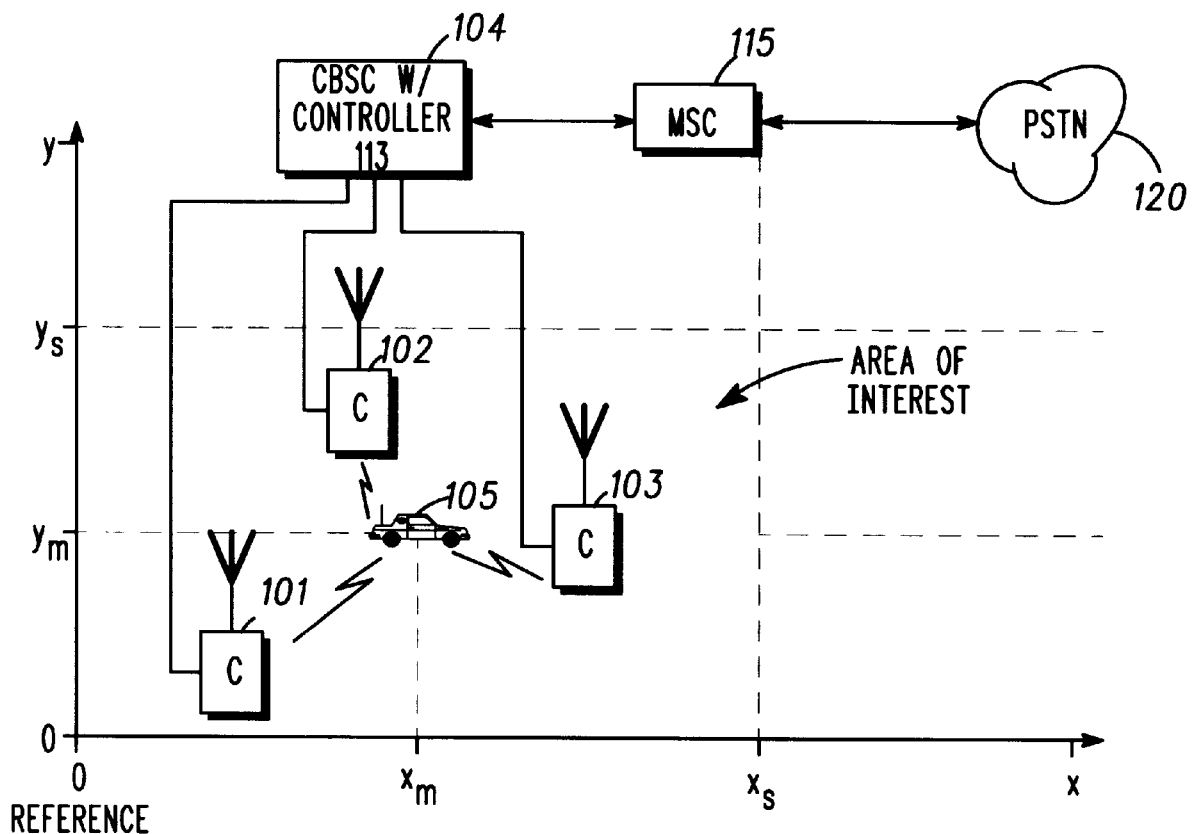
FIG. 4 generally depicts an exemplary parameter mesh calculation space for the system of FIG. 1 in accordance with the invention.

This mesh calculates, in consideration of, inter alia, mobile station speed, delay spread, likely handoff connections (hereafter called "the conditions") the power that would be required to transmit from the serving cell to a mobile station at the mobile station's vertex, shown as $x_m, y_m$ in FIG. 4. The power is determined by a predetermined voice quality in terms of frame erasure rate (FER). These frame erasure rates are also predetermined by either computer characterization or laboratory characterization, of the radio links of the system. Because it is power required to close the link at the desired quality, it can also be used to determine a margin for each and every point in the system relative to some physical limitation (like the size of a power amplifier, or PA, in the base-station or a limit on each traffic channel transmit power). For example, the power required may be 8 watts (W); if it is planned to limit the traffic channel power to 2 W, then the required power is 6 dB over the limit.

Reverse Link (Mobile Station to Base-station) Power Requirement

The same idea as the forward power required mesh, based on the conditions. Because it is power required, it can be applied after the fact to any size PA, as will be described below.

Number of Useful Pilot Signals

The number of useful pilots mesh evaluates, under the conditions, the number of pilots (one is possible from each sector) which at each vertex of the mesh would be useful (i.e., could be used for soft handoff). This parameter is determined by calculating the IS-95 quantity Ec/Io and, if it passes a preset threshold, counting it. In this way the values in the mesh are integers representing the number of connections which could be had at the given location, and irrespective of the number of connections the mobile station is actually capable of. In fact, if more pilots are useful than the mobile station can handle, this may be troublesome.

Ec/Io, also Known as the Best Pilot Signal

This mesh holds a calculation of, in consideration of the conditions, the Ec/Io of the pilot determined to be the best in Ec/Io terms in each location. A good pilot is essential for good forward link communications, and this mesh indicates whether it is even possible to receive a good pilot. What is good can, as in the case of the other meshes, be imposed afterward, as this mesh holds the values whatever they are.

As one of ordinary skill in the art will appreciate, a number of other parameter meshes can be created to gain a better understanding of the CDMA communication system 100. The parameters related to these meshes include, but are not limited to, load imbalance which describes the balance between received power of adjoining cells, relative usable to non-usable cell power on the forward link, and performance of the paging channel. The relative usable to non-usable cell power describes the fraction of total cell (all cells in system) power as measured at a mobile station's antenna which is recoverable by the mobile station (with respect to total cell power plus all other noise and interference not produced by the cells in the system). The relative usable to non-usable cell power is defined by the variable "iorioc".

The method of calculating the meshes is the same when either a space epoch or time epoch method is used.

Space Epoch

Space epoch is defined as having a plurality of base-stations (e.g., base-stations 101–103) and mobile stations (e.g., mobile station 105) in the system under test and performing an interactive calculation in controller 113 to bring each forward link and each reverse link traffic channel to its best value of mean transmit power in light of all other traffic channels and a large number of other physical parameters. Having finished that calculation, the communication system 100 is considered stabilized for that mobile station and base-station spatial configuration.

Figure 5:
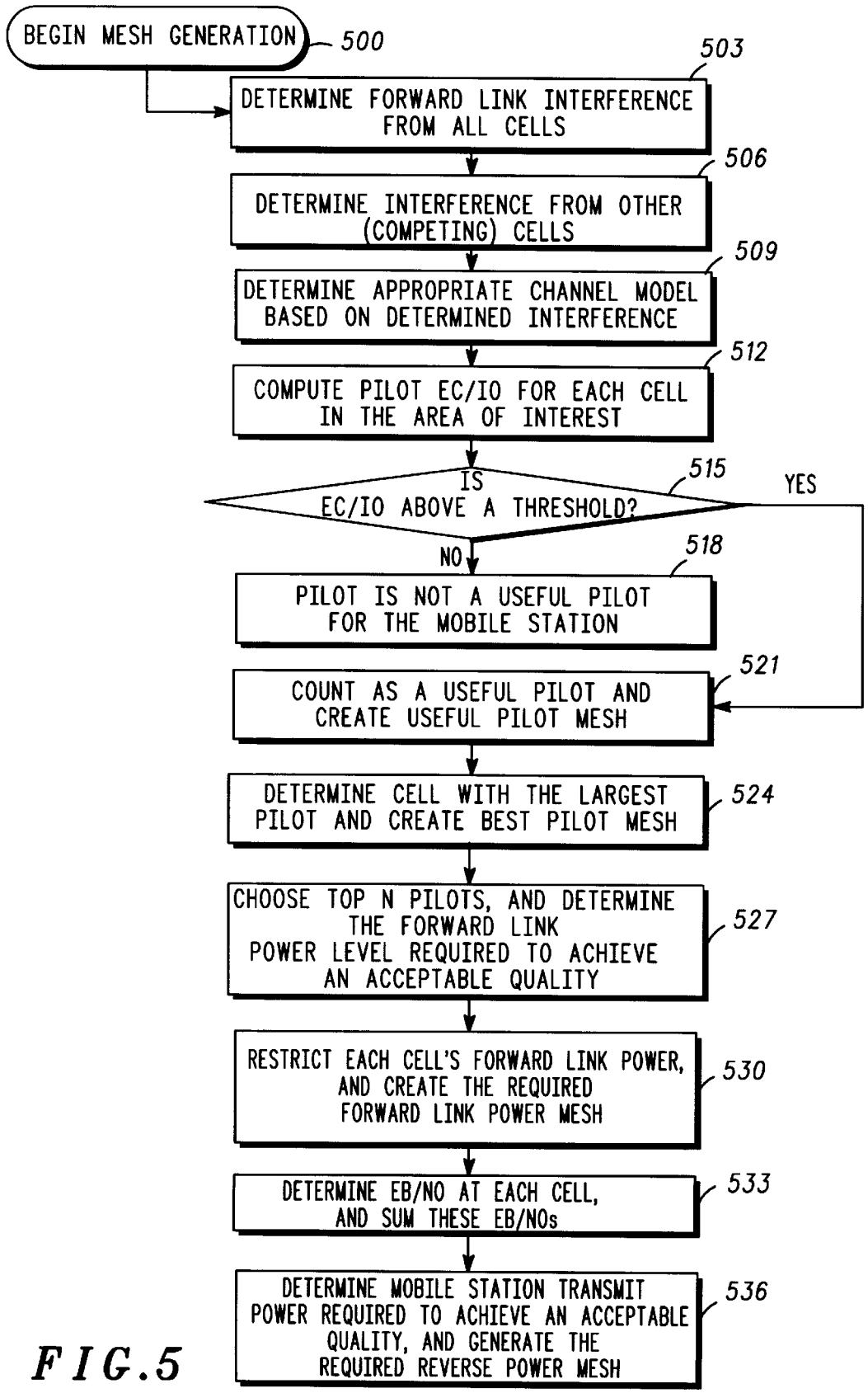
FIG. 5 generally depicts, in flow diagram form, the steps taken by the controller of FIG. 1 to determine various parameter meshes for use in system control in accordance with the invention.

Next, the space epoch mesh is calculated by imagining the placement at each vertex of the mesh just one more mobile station (which does not impact the system in any way) and calculating the parameter of interest at each point in consideration of all system noises, the best serving base-station, or base-stations if soft handoff would be encountered, in light of the delay spread at that vertex point and a reported speed for the mobile station. For each x,y location of the grid overlaid on the provider's system coverage area, the controller 113 performs the steps as depicted in FIG. 5. First, the controller 113 determines, at step 503, the total forward link interference from all cells ($I_t$), then determines, at step 506, interference from other competing systems and/or non-provider's noise sources ($I_{np}$) allowing for mobile station adjustments to mitigate their effect (e.g., attenuation in the mobile station's receiver front-end to mitigate intermodulation distortion due to competing system interference) to produce a total interference represented by $I_t' = I_t + I_{np}$.

The controller 113 then determines, at step 509, the channel model due to delay spread (number of signal paths between server and remote unit), represented by:

fng_frc_fwd[0,i]=fraction of total power recovered or FRP (with respect to the mobile station's antenna) by the mobile station finger for strongest signal path corresponding to cell i;

fng_frc_fwd[1,i]=fraction of total power recovered (with respect to the mobile station's antenna) by the mobile station finger for second strongest signal path;

fng_frc_fwd[n,i]=fraction of total power recovered (with respect to the mobile station's antenna) by the mobile station finger for nth strongest signal path;

As defined here, the number of different cells to which the n strongest signal or forward links correspond is equal to the number of forward links. Cells or sectors are defined with respect to IS-95A (mentioned above) with a distinct pilot PN offset.

The controller 113, then computes, at step 512, the pilot Ec/Io (pilot_ecio) and pilot Ec/No (met) for each forward signal path from each cell i, where:

$Dr = N_o W_{mt} + I_t$ is the total interference at the mobile station antenna and $N_o W_{mt}$ is effective thermal noise due to remote unit receiver);

$EcIo_{13}$ flat(i)=(Ppilot(i)/$D_r$) is the strongest pilot Ec/Io not accounting for FRP for cell i as measured at the mobile station antenna;

EcIo(i)=(fng_frc_fwd[0,i]*EcIo_flat(i)) is the strongest pilot Ec/Io for cell I accounting for FRP; pilot_ecio[i]=EcIo(i) is the strongest Ec/Io path for cell i;

pilot_ecio1[i]=EcIo_flat(i)*fng_frc_fwd[1,i];

pilot_ecio2[i]=EcIo_flat(i)*fng_frc_fwd[2,i];

Dra=It-fng_frc_fwd[0,i]*Pcell(i)+NoWmt.

Pcell(i) is power receiver at the mobile station's antenna only from cell i. Other variables are defined as:

Drb=It-fng_frc_fwd[1,i]*Pcell(i)+NoWmt;

Drc=It-fng_frc_fwd[2,i]*Pcell(i)+NoWmt;

met[i]=fng_frc_fwd[0,i]*Ppilot(i)/Dra;

met1[i]=fng_frc_fwd[1,i]*Ppilot(i)/Drb;

met2[i]=frg_frc_fwd[2,i]*Ppilot(i)/Drc;

Ppilot(i) is the pilot power received from cell i as measured at mobile station's antenna.

At this point, the controller 113 tests, at step 515, whether the computed Ec/Io is above a threshold (typically in the range of −12 to −20 _dB). If the result of the test at step 515 is negative, then the process flows to step 518 where the pilot is considered not to be useful for the mobile station. If the result of the test at step 515 is positive, then the controller 113 counts the number of cells with pilot Ec/Io above an arbitrary threshold and saves this quantity for creating the "number of useful pilots" mesh, step 521. Based on the above equations, the controller 113 then determines the cell with the largest pilot Ec/Io signal path and saves this quantity for creating the best server mesh. Alternatively, the controller 113 computes the reverse link Eb/No and saves this quantity for creating the best server mesh for the reverse link.

At this point, the controller 113 determines, at step 524, the path of the largest pilot signal Ec/Io and saves this quantity for creating the "best pilot signal–Ec/Io" mesh. Given the number of forward signal paths (each useful pilot can have k signal paths associated with it due to delay spread) and their respective signal strength, the controller 113 chooses, at step 527, the top n. The controller 113, given the number of available demodulators (fingers) in the mobile station 105, computes, also at step 527, the required forward link power levels from each cell needed to achieve an acceptable frame erasure (quality) level accounting for the mobile station's speed, "iorioc" (as described previously) and restrictions on successfully assigning fingers to available signal paths.

With the above information, the controller 113 chooses the top n signal paths in terms of pilot Ec/Io, where n is equal to the number of demodulators (fingers) available in the mobile station.

In the preferred embodiment, n=3. From this information, the following variables are determined:

ecio_0=pilot Ec/Io of strongest path (e) from cell k;

ecio_1=pilot Ec/Io of second strongest path (f) from cell l;

ecio_2=pilot Ec/Io of third strongest path (g) from cell m;

speed=speed of the mobile station;

MaxPilot=the Ec/Io level corresponding to largest pilot signal path (largest Ec/Io) as measured at the mobile station antenna; and iorioc=the sum (Is_tot) of usable cell power as measured at the mobile station antenna for the strongest paths to which fingers were able to be assigned divided by the sum of the total received power (Itot) at the mobile station antenna minus Is_tot.

For the case where the mobile station has three fingers and there are at least 3 fingers that are usable (i.e., fingers can be assigned because the signal path strengths are large enough in term of Ec/Io) forward signal paths for which are chosen the three strongest (e,f,g) corresponding to cells (k,l,m), then:

Is0[k]=fng_frc_fwd[e,k]*Pcell(k);

Is1[l]=fng_frc_fwd[f,l]*Pcell(l);

Is2[m]=fng_frc_fwd[g,m]*Pcell(m);

Is_tot =Is0[k]+Is1[l]+Is2[m];

iorioc=Is_tot/(Itot-Is_tot);

EbNo_tgt=f(MaxPilot, ecio_0/ecio_1,ecio_1/ecio_2, speed, iorioc, desired frame quality level) where f() can be a Eb/No lookup table indexed by the above parameters;

Ptarget_fwd=MaxPilot*EbNo_tgt/(met[e,k]+met[f,l]+met[g,m]) is the required forward power for each forward path.

Note that this implementation assumes all forward paths have equal transmission (voice or traffic channel) power-to-pilot power ratio.

Next, the controller 113 restricts, at step 530, each cell's forward link power (Ptarget-fwd) based on an allowable minimum and maximum levels which may differ from cell to cell. The controller 113 then saves the Ptarget_fwd for each x,y to create, also at step 530, the forward power mesh.

For each forward signal path corresponding to a different cell (forward link), the controller 113 next computes, at step 533, the Eb/No (EbNo($i_{cd}$)) for the corresponding reverse signal paths at each of the cell's antenna connectors assuming that the mobile station is transmitting at 1 milliWatt (mW-Pcur). These reverse signal path Eb/No's (EbNo_sum) are then summed, also at step 533. The controller 113 then computes, at step 536, the required mobile station transmit power needed to attain a target Eb/No (EbNo_rtar) which is necessary to maintain a desired frame quality level after decoding frames at the serving cell (BTS) or after post-frame selection at a location using the frames from all the serving cells (CBSC) in the case of soft handoff. As an example, using the case of two-way soft handoff with cells k and l having two delay spread paths per antenna:

EbNo_sum=EbNo_rtch[k11]+EbNo_rtch[k12]+EbNo_rtch[k21]+EbNo_rtch[k22]+EbNo_rtch[l11]+EbNo_rtch[l12]+EbNo_rtch[l21]+EbNo_rtch[l22]

where $i_{cd}$=reverse signal path d at antenna c corresponding to cell i;

EbNo_rtch[$i_{cd}$]=(fng_frc_rev[$i_{cd}$]+fng_frc_rev[$i_{cd}$])Pcur(u)T(u,$i_{cd}$)PG/Drr($i_{cd}$);

Drr($i_{cd}$)=NoWc[$i_{cd}$]+Nbackground [$i_{cd}$]+It_rev[$i_{cd}$];

PG=processing gain (chip rate/information rate);

Pcur(u)=mobile station u's current transmit power with respect to mobile station's antenna (1 mW);

T(u,icd)=transmission gain between mobile station u and antenna c of cell i for signal path d;

It_rev[$i_{cd}$]=total interference due to all other mobile station's in system plus noise (thermal and non-CDMA) measured at cell i's antenna connector c;

fng_frc_rev[$i_{cd}$]=fraction of total power recovered or FRP (with respect to serving cell i's antenna connector c by cell's demodulator (finger) for signal path d;

NoWC[$i_{cd}$]=thermal noise power due to serving cell i's receiver with respect to antenna c;

Nbackground [$i_{cd}$]=noise due to non-CDMA sources (e.g. man made noise or analog interference);

EbNo_tgt=h(desired frame quality, speed, 100W);

EbNo_tgt2=h(desired frame quality, speed, power headroom);

Ptarget_rev1(u)=EbNo_tgt+Pcur(u)−EbNo_sum;

power headroom=difference between mobile station's maximum transmit power and required transmit power Ptarget_rev1(u); and Ptarget_rev2(u)=EbNo_tgt2+Pcur(u)-EbNo_sum.

At this point, the controller 113 saves the required remote unit power level needed to achieve a desired frame quality level (Ptarget_rev2(u)) for creating, also at step 536, the required reverse power mesh.

Upon completion of the parameter mesh generation, all mobile stations are moved to new locations and first the convergence, then the mesh calculation, is repeated. This makes a mesh set, for each parameter, over a set of mobile station locations, but reflecting the potential condition at each location in the system, regardless of whether a mobile station was located there, and how many times that would have happened over the set of mobile station locations. Each set of mobile station locations are referred to as a "drop", as if the mobile stations were just dropped into the area of interest.

Time Epoch

When a mesh set is created over a time epoch, the mesh computations themselves are carried out in exactly the same way. The difference is the way the transmit powers at the mobile station and base-station come to be. In this case, the transmit powers are not converging to their best mean value, but are produced by a simulation which models the actual time sequential evolution of the system, with time sequential power control and control messaging expressed.

The parameter meshes are calculated after some time interval, from the minimum time resolution of the simulation to several seconds or minutes. In this case, the order of the meshes matters. The meshes of these mesh sets can be considered indexed, not only by a set of mobile station locations, but by increments in time. Hence, when a particular parameter of interest is "bad", it is known for how long this parameter was bad, not only how often it happens. Additionally, the time epoch meshes, calculated from realistic system flaws (e.g., being connected to a non-optimal site or set of sites) includes the noise effects of those system flaws.

Once the parameter meshes are determined, an efficient manner of evaluating the parameters is implemented. Several mesh "tools" to evaluate the parameters are explained below.

Single Mesh Tool

If a hard threshold can be set (e.g., 2 W forward link power), then the mesh set can be manipulated by checking each vertex for each mesh, and setting a pass/fail criterion. As an example, if the forward power mesh is used and it is desired to know what fraction of the time the required power exceeds 2 W, each mesh can be tested and for each mesh that passes (that is, requires more than 2 W), that mesh is counted. If N of the meshes pass for a given vertex at x1,y1, and there are M meshes, then over the whole set the criterion is passed N/M of the time at vertex x1,y1. This process is repeated for all vertices xi,yj, where i is the index for x in the mesh and j is the index for y. In this way, the entire mesh set for a particular parameter is reduced to a single mesh, where the values in the mesh represent the probability that a certain criterion is passed. This can be done equally well for meshes either from the space or time epochs, but the time mesh set will include additional corrections for realistic performance.

If the criterion is not passed some predetermined fraction of the time, performance in this location is considered unacceptable and the controller 113 takes action to alter the system performance during operation. In the case of the forward link calculation, all the forward link and reverse link powers of system are saved in a predetermined pathloss file within the controller 113. This file may be pre-measured or calculated as is well known in art. If the power required to transmit into an area is beyond the capability of the transmitting power amplifier (e.g., the transmitter 300 of base-station 102 of FIG. 3), then the noise impinging on that area can be computed by the controller 113. This is because, as shown in the calculations above, the determination of power required includes all traffic channel powers as well as all pilot/page/synchronization channel powers from all base-stations in the system. It may be possible to reduce the pilot/page/synchronization channel powers from one or several base-stations in the system and thereby reduce noise in the area having the coverage problem. The power required from the base-station transmitter may then be able to deliver enough power for a satisfactory connection.

The method of reducing power is as follows. First the major noise terms in the expression for those regions determined "not satisfactory" are found. The pilot/page/synchronization channel powers for the base-station having the largest noise term is lowered by a predetermined amount, for example 3 dB. In consideration of such a reduction, the calculation is repeated by re-evaluating the whole system and repeating the mesh calculation. If the area previously considered to be not satisfactory is now satisfactory, AND either no new unsatisfactory area is detected, or a smaller unsatisfactory area is created, then this indicates that the pilot/page/synchronization channel powers were set too high for conditions of the moment. In this manner, improved CDMA system control occurs in accordance with the invention.

The importance of the areas, rather than their size, may also be considered in accordance with the invention. Located within the memory of the controller 113 is a map of the cellular system's coverage area. Each sub-section of the map can be assigned a number representing its relative importance to the system as a whole. For example, from the perspective of the owner of the communication system, a downtown area is likely to be more important than an area over a cemetery. After a parameter mesh of the area is generated and an evaluation performed taking into account the pilot/page/synchronization channel powers, it may be that an area deemed unacceptable and altered accordingly (as described above) is in fact larger than the repaired area but is less important. In this scenario, a change to the system based on the importance of the area is executed in accordance with the invention.

Important to note is that the method of characterizing coverage and loading in a CDMA communication system provides improved system control by, inter alia, being capable of generating a new parameter mesh (or sets of parameter meshes) immediately after a change in the system has occurred, and re-evaluating the mesh (or meshes) to determine if the overall performance of the system has improved or degraded. As such, should a power adjustment on the signal having the largest noise worsen some other important aspect of the communication system, then an adjustment on the next noise source is tried. Adjustments of still other noise sources may be tried in combination until the problem is fixed or an alarm reports the recurring problem to a system operator. The reporting alarm could take many forms, including a map which shows the mesh calculations and highlights (by brightness, color, or other such means) the area which is unacceptable and cannot be fixed. Similarly, an ASCII message could be flashed to the system operator indicating an irreparable problem in the designated area.

Another method of characterizing coverage and loading in a CDMA communication system to improve system control is to evaluate which base-station(s) in the parameter mesh contribute the largest forward link power in a given area, and remove that base-station's contribution from the calculation. In effect, the power from the interfering base-station would be subtracted from the traffic channel noise. If this fixes the problem in the unacceptable region in the manner described above, then the controller 113 can limit the number of connections allowed to that interfering base-station. After some period of time, it may be that re-evaluation (through re-generation of parameter meshes) of the original troubled area shows no problem (perhaps due to a reduction in base-station transmission from other parts of the system). In this scenario, the number of traffic connections from the interfering base-station can be allowed to rise again.

In a similar way the same tool can be applied to the useful pilots mesh. For example, it is desirable to determine how often the number of useful pilots exceeds the available RAKE demodulating fingers in the mobile station. When the number of pilots in a particular area exceeds that which is useful to the mobile station 105, the additional signals are only added noise to the receiver and are destructive to signal quality. On the other hand, it may be that only two pilots are present, but due to delay spread on one of the pilot signals, the three fingers in the mobile station 105 are in use. In this scenario, further signals may be destructive to the mobile station's received signal quality. If this is the case, as in the example above, the controller 113 is aware of all the pilot signal powers, and therefore all the noise powers, in the system. Again, the largest noise signal, represented by the total power from another base-station is determined and that base-station's pilot/page/synchronization channel powers is lowered. By changing the number of usable pilots or the amount of usable signal-to-noise ratio after the system is re-evaluated without creating another area of unacceptable performance (of equal or greater importance), CDMA system control improves in accordance with the invention.

As another example, the reverse power mesh can be used to determine whether the coverage from a certain region of the system is unacceptable in the reverse link. This can occur when the noise in the receiver 203 of base-station 102 cannot be overcome by the transmitter 200 of the mobile station 105 and thus deliver the appropriate connection quality. This noise can be contributed from around the system, not just the cell being served by the base-station 102. The controller 113 has knowledge of the location of each mobile station in the system and their corresponding connections and contributions, thus the mobile stations which contribute the majority of noise to the base-station in a particular area are known. With this knowledge, the controller 113 can instruct the contributing mobile stations to reduce their power until the area in question is satisfactorily covered. This can then serve as a basis to limit the connections to/from the base-stations of the offending cells until conditions change such that these connections no longer cause a problem in the troubled area. Since the elimination of connections will have no other negative impact on any coverage, there is no need to evaluate other areas, unlike the forward link case.

The operators of the cellular system may make note, or the controller 113 may track alarms or incidences of problem areas, and if during the course of operation an area or areas become unacceptable for a predetermined fraction or time of the work day, then the parameter meshes taken individually or in groups can yield an indication of the type and/or severity of the problem. The problems can then be remedied by the addition of base-stations, use of different antennas, etc. How this interpretation is performed is described in further detail below.

Multiple Mesh Tool

CDMA's greater complexity means that it is often beneficial to simultaneously evaluate more than one mesh statistically. By evaluating more than one parameter mesh at a time, a greater overall understanding of the CDMA system can be obtained.

For example, a first combination of meshes which would be checked are the forward and reverse link power required meshes. Because a cellular communication is two-way, both the forward and reverse link power need to be good. If either is bad, it is highly likely that the communication is bad. With this in mind, the corresponding mesh points on each mesh are checked. Important to note is that the test could use different criterion for each mesh. For example, the forward link power required may be less than 33 dBm, while the reverse link power required may be less than 20 dBm. If BOTH are true at a point, this is a pass condition for that vertex. Now, as previously stated, the probability of a pass for each vertex is N/M, and the two meshes have (in effect) been reduced to a single probability mesh. Areas of the resulting mesh failing the criterion are candidates for further study.

For example, areas which are simultaneously unacceptable on the reverse link mesh and the best Ec/Io mesh, particularly under light loads, often can be seen as suffering from a "pathloss problem". That is, there is likely no base-station in the CDMA system which can serve that region with acceptable quality. However, as the CDMA system begins to load, such regions suffering from the "pathloss problem" may slowly disappear. If the controller 113 is unable to decrease the major interferers to an acceptable level, then the region should be alarmed to a system operator (as described above) because a system re-design is likely required.

As another example, when the best Ec/Io mesh shows an unacceptable value (for example, a value below −13 dB) and the number of good pilots mesh indicates a "large" number of pilots (for example, six), these pilots are likely to be interfering with each other and creating a problem specific to this scenario - that none of the pilots is seen as good. This is not a "pathloss problem" as described above but rather the pathloss is too low for too many base-stations from the area in question. This is known to be a troublesome condition for prior art CDMA control systems. To mitigate this problem in accordance with the invention, one (or more) of these pilots are reduced in power. If this cannot be done without degrading some other important area, then a base-station (or base-stations) may have to be moved to repair the problem. These new base-station locations can be re-evaluated by the controller 113 as described above.

Time Mesh Tool

In this case, a particular mesh set my be searched for a particular condition being met for a particular number of meshes in sequence, which, when the meshes are run over the time epoch, represents a number of seconds. This will not work when the meshes are created over the space epoch alone.

As an example, consider the time periods when the forward or reverse link power required goes above the available power. For short time periods, this condition may be acceptable; for longer time periods, this condition is clearly unacceptable. By including time in the evaluation, the final resulting mesh depicts the probability of that particular event occurring at each location. There are many ways this event could be reported, including reporting the number of occurrences, the total duration of occurrences, the total fraction of time of the occurrences, etc.

System control based on this time mesh tool is similar to that described above, and is only a different way of looking at what is deemed "unacceptable". In the above discussions, it was implied that average performance of the links in question were used to define the meaning of "unacceptable". But in fact averages over long times may hide shorter periods of seriously unacceptable performance, while the users of a cellular system are in fact likely to respond in a subjectively negative way to short periods of poor service.

With this mesh tool, the criteria usable here could be N periods of "poor" service, or duration at least t seconds in a longer period of T seconds. In a much more simple configuration, any period or at least t seconds of poor service may be the condition. These definitions of unacceptable service and/or quality are adjustable in the controller 113.

In prior art CDMA controllers, "coverage" was represented as a function of a single variable such as pathloss or carrier-to-interference ratio. By implementing parameter meshes in accordance with the invention, not only is pathloss accounted for but also delay spread, power control for all mobile stations in the system, variations in radio sensitivity due to mobile station speed, soft handoff states throughout the system, receiver efficiency in recovering energy and other variables for both forward and reverse links individually and/or simultaneously. In the time epoch, the time evolution of the system is used, leading to enhanced knowledge of link quality over simple statistical methods used in the past. Furthermore, calculations are produced over the entire area of interest.

Accordingly, it is intended that the invention not be limited by the foregoing description of embodiments, but to embrace all such alterations, modifications, and variations in accordance with the spirit and scope of the appended claims. While the invention has been particularly shown and described with reference to a particular embodiment, it will be understood by those skilled in the art that various changes in form and details may be made therein without departing from the spirit and scope of the invention. The corresponding structures, materials, acts and equivalents of all means or step plus function elements in the claims below are intended to include any structure, material, or acts for performing the functions in combination with other claimed elements as specifically claimed.

What we claim is:

1. A method of controlling a communication system, the method comprising the steps of:

calculating at least one parameter mesh corresponding to a parameter related to the communication system at each x,y coordinate of a grid over an area of interest, the parameter related to the communication system comprising forward and reverse power requirements, a number of useful pilot signals and a best pilot signal;

evaluating the at least one parameter mesh to generate a control signal effecting the parameter related to the communication system; and controlling the communication system based on the generated control signal.

2. A method of controlling a communication system, the method comprising the steps of:

calculating a plurality of parameter meshes corresponding to a plurality of different parameters related to the communication system at each x,y coordinate of a grid over an area of interest, the plurality of different parameters related to the communication system comprising forward and reverse power requirements, a number of useful pilot signals and a best pilot signal;

combining predetermined parameter meshes to generate predetermined control signals; and controlling the communication system based on the generated predetermined control signals.

3. A method of controlling a code division multiple access communication (CDMA) system, the method comprising the steps of:

determining forward link power requirements for all base-stations in an area of interest;

determining, based on the determined forward link power requirements, the base-station which contributes the largest forward link power; and limiting the number of mobile station connections to that base-station so that its forward link power contribution with respect to the total forward link power of all base-stations is diminished.

4. The method of claim 3, wherein the number of connections to the base-station of interest are allowed to increase based on a re-evaluation of the base-station's effect on the communication system.

* * * * *